United States Patent
Gou et al.

(10) Patent No.: US 11,199,483 B2
(45) Date of Patent: Dec. 14, 2021

(54) METHOD FOR EXPERIMENTALLY DETERMINING INFLUENCE OF ACID LIQUOR ON YOUNG'S MODULUS OF COMPACT CARBONATE ROCK

(71) Applicant: SouthWest Petroleum University, Sichuan (CN)

(72) Inventors: Bo Gou, Sichuan (CN); Jianchun Guo, Sichuan (CN); Zhuang Liu, Sichuan (CN); Xiao Li, Sichuan (CN); Mingyong Zeng, Sichuan (CN); Li Zhan, Sichuan (CN)

(73) Assignee: SOUTHWEST PETROLEUM UNIVERSITY, Sichuan (CN)

( * ) Notice: Subject to any disclaimer, the term of this patent is extended or adjusted under 35 U.S.C. 154(b) by 164 days.

(21) Appl. No.: 16/627,037

(22) PCT Filed: Apr. 3, 2018

(86) PCT No.: PCT/CN2018/081692
§ 371 (c)(1),
(2) Date: Dec. 27, 2019

(87) PCT Pub. No.: WO2019/119676
PCT Pub. Date: Jun. 27, 2019

(65) Prior Publication Data
US 2020/0124511 A1 Apr. 23, 2020

(30) Foreign Application Priority Data
Dec. 21, 2017 (CN) .......................... 201711394610.4

(51) Int. Cl.
*G01N 3/08* (2006.01)
*G01N 33/24* (2006.01)

(52) U.S. Cl.
CPC ............... *G01N 3/08* (2013.01); *G01N 33/24* (2013.01); *G01N 2203/0019* (2013.01); *G01N 2203/0075* (2013.01)

(58) Field of Classification Search
CPC .. G01N 3/08; G01N 33/24; G01N 2203/0019; G01N 2203/0075
(Continued)

(56) References Cited

U.S. PATENT DOCUMENTS

2014/0174168 A1 6/2014 Amanullah et al.

FOREIGN PATENT DOCUMENTS

CN 101963056 A 2/2011
CN 102011580 A * 4/2011
(Continued)

OTHER PUBLICATIONS

Translation of CN-102011580-A (provided by Applicant) (Year: 2011).*

*Primary Examiner* — Nathaniel T Woodward
(74) *Attorney, Agent, or Firm* — Muncy, Geissler, Olds & Lowe, P.C.

(57) ABSTRACT

The present invention discloses a method for experimentally determining the influence of acid liquor on the Young modulus of compact carbonate rock. The method comprises the following steps: (1), selecting a standard core of compact carbonate rock for use, carrying out a uniaxial compressive strength experiment to establish an empirical relationship between the uniaxial compressive strength and the Young modulus of the compact carbonate rock; (2), selecting a full-diameter core in a target work area for use, carrying out a rock scratching experiment by using a rock scoring instrument, testing the compressive strength of the core, and acquiring the Young modulus of the core before acid treatment; (3), soaking the acid liquor and the core in a high- (Continued)

temperature and high-pressure reactor for a soaking reaction; and (4), carrying out a scratching experiment again on the core soaked with the acid liquor in the original scratching experiment position, testing the compressive strength of the core, acquiring the Young modulus of the core after acid treatment, and determining the influence of the acid liquor on the Young modulus of the compact carbonate rock. The method disclosed by the present invention is reliable in principle, and simple and convenient in operation. The influence of the acid liquor on the Young modulus of the compact carbonate rock under reservoir conditions is authentically evaluated, and the acid fracturing transformation effect of the compact carbonate rock is further improved.

5 Claims, 2 Drawing Sheets

(58) Field of Classification Search
USPC .......................................................... 73/818
See application file for complete search history.

(56) References Cited

FOREIGN PATENT DOCUMENTS

| | | | |
|---|---|---|---|
| CN | 102011580 A | 4/2011 |
| CN | 102288986 A | 12/2011 |
| CN | 103674679 A | 3/2014 |
| CN | 105021458 A | 11/2015 |

* cited by examiner

METHOD FOR EXPERIMENTALLY DETERMINING INFLUENCE OF ACID LIQUOR ON YOUNG'S MODULUS OF COMPACT CARBONATE ROCK

TECHNICAL FIELD

The present invention relates to a method for experimentally determining the influence of acid liquor on the Young's modulus of a compact carbonate rock in the field of petroleum engineering, and quantitatively determining the influence of acid liquor on the Young's modulus of the compact carbonate rock through experiments, to provide a basis for accurate calculation and evaluation of the conductivity of an acid-fractured crack under formation conditions, thereby improving the accuracy of the design of the compact carbonate rock acid-fracturing scheme, and achieving high-efficiency acid fracturing transformation of the compact carbonate rock.

BACKGROUND

In recent years, China has successively discovered a large number of compact carbonate rock oil and gas reservoirs, which have gradually become one of the hotspots of oil and gas exploration and development, such as the Daniudi gas field in the marine Ordos Basin, the Jingbian gas field, and the Sinian Moxi-An Yue gas field in the Sichuan Basin, Chuanxi Leikoupo gas reservoir, etc.; and compact oil carbonate rocks in the lacustrine Bohai Bay Basin, Qaidam Basin, and Junggar Basin. Due to the compact reservoir which usually has a porosity of less than 10% and permeability of less than $1.0 \times 10^{-3}$ µm$^2$, it is difficult to obtain industrial oil and gas naturally. Acid fracturing is an important technical means for building and increasing production of such reservoirs (Wei Xinshan, Chen Hongde, Zhang Daofeng, et al, Characteristics of Compact Carbonate Rock Reservoirs and Exploration Potential of Natural Gas-Taking the Ordovician Majiagou Formation in the eastern Yishan Slope of Ordos Basin as an example [J]. Petroleum Exploration and Development, 2017,44(3): 319-329).

Acid fracturing means that acid liquor is extruded into a reservoir under a pressure higher than a fracturing pressure of the reservoir or a closing pressure of a natural crack to form a crack in the reservoir, and a chemical reaction occurs between the acid liquor and the rock on the crack wall to non-uniformly etch the rock on the crack wall, thereby forming a grooved or uneven etched crack. After the completion of the construction, the crack is not completely closed to finally formed an acid-etched crack with certain geometrical size and conductivity, such that the production of an oil and gas well is increased (Li Yingchuan, Oil Production Engineering [M]. Petroleum Industry Press, 2009). The conductivity is one of the important factors affecting the acid fracturing effect. It is mainly affected by the shape of the acid-etched crack, the mechanical strength of the rock subjected to acid etching, the closing stress, etc. The mechanical strength of the rock subjected to acid etching is an important factor for determining the conductivity of the crack under the closing stress. Two important parameters for characterizing mechanical characteristics of the linear elasticity of carbonate rock are Poisson's ratio and Young's modulus. Numerical simulation researches show that the Poisson's ratio has little effect on the conductivity of acid-etched cracks, while the Young's modulus has obvious influence on the conductivity. Especially under high closing stress conditions, the higher the Young's modulus of the rock subjected to acid etching, the higher the conductivity of the corresponding acid-etched crack (Deng J, Mou J, Hill A D, et al. A New Correlation of Acid-Fracture Conductivity Subject to Closure Stress [J]. SPE Production & Operations, 2011, 27(2): 158-169), and therefore, it is crucially important to determine the Young's modulus of the rock subjected to acid fracturing.

In the acid fracturing process, due to the chemical reaction of acid and rock, the acid liquor will deteriorate the mechanical strength of the rock (such as reducing the Young's modulus). The change in the Young's modulus of the rock subjected to acid fracturing is often determined by experimental methods (He Chunming, Guo Jianchun, Mechanism Research of Influence of Acid Liquor on Mechanical Properties of Limestone [J]. Journal of Rock Mechanics and Engineering, 2013(s2):003016-3021). For carbonate rock with pore development, the following two testing methods are often used: first, a standard core is selected from a research area to test the Young's modulus of the core that has not reacted with acid by using triaxial rock mechanics test; another core is then selected, acid liquor displacement is used to simulate the influence of acid on rock during acid fracturing, and then the rock's Young's modulus after acid displacement is tested and compared with the Young's modulus of rock that has not previously reacted with acid (He Chunming, Guo Jian Chun, Mechanism Research of Influence of Acid Liquor on Mechanical Properties of Limestone [J]. Journal of Rock Mechanics and Engineering, 2013(s2):003016-3021). The second testing method is as follows: the variation in the propagation velocity of sound waves in rock before and after acid liquor displacement is tested to characterize the change in the Young's modulus in the tested rock (Barri A, Mahmoud M, Elkatatny S. Evaluation of Rock Mechanical Properties Alteration during Matrix Stimulation with Chelating Agents [J]. Journal of Energy Resources Technology, 2016, 138(3): 1-7). However, for compact carbonate rock, the acid liquor is difficult to be displaced into the core. The acid liquor reacts only on the end surface of the core. The acid liquor is mainly responsible for damaging the local mechanical properties of the rock. The triaxial rock mechanics test or the acoustic velocity testing method is difficult to reflect the change in local rock mechanics properties. On the other hand, the triaxial rock mechanics property test is a destructive test, that is, after the same rock sample is tested for rock mechanics properties, subsequent acid liquor displacement experiments and rock mechanics properties experiments cannot be carried out, so the conventional triaxial mechanical test method is difficult to truly reflect the change in the Young's modulus of the same rock sample before and after acid treatment, which is not conducive to quantitative evaluation of the influence of the acid liquor on the Young's modulus of the compact carbonate rock, and directly affects the accuracy in calculation of the conductivity of acid-etched cracks in the acid fracturing design.

SUMMARY

The object of the present invention is to provide a method for experimentally determining the influence of acid liquor on the Young's modulus of compact carbonate rock. The method is reliable in principle and easy to operate, and the Young's modulus of the same rock sample before and after acid treatment is tested, which is beneficial to authentically evaluating the influence of the acid liquor on the Young's modulus of the compact carbonate rock under reservoir conditions, thereby improving the calculation accuracy in the conductivity of acid-fractured and acid-etched cracks of carbonate rock, and further improving the acid fracturing transformation effect of the compact carbonate rock. The method has broad market prospects.

To fulfill said technical objective, the present invention provides the following technical solution:

firstly, selecting a standard core of a compact carbonate rock in a target work area for use, and carrying out a uniaxial compressive strength experiment to establish an empirical relationship between the uniaxial compressive strength and the Young's modulus of the compact carbonate rock; then, selecting a full-diameter core from the target work area, carrying out a rock scratching experiment by using a rock scoring instrument to test the compressive strength of the core, and acquiring the Young's modulus of the sample rock before acid treatment according to the empirical relationship between the compressive strength and the Young's modulus; next, sealing a portion of the full-diameter core, which never contacts the acid liquor, with potting glue, determining experimental conditions according to a reservoir temperature in the acid fracturing process, a fluid pressure in the crack, and an acid injection time, selecting an acid liquor system for acid fracturing in the field for use, and placing the acid liquor and the rock in a high temperature and high pressure reactor for a soaking reaction; and finally, carrying out a scratching experiment again on the rock soaked with acid to test the compressive strength of the core, and acquiring the young's module of the sample rock after acid treatment according to the empirical relationship between the compressive strength and the Young's modulus; and comparing the Young's modulus of the sample core with the Young's modulus of the sample core before acid treatment to determine the influence of the acid liquor on the Young's modulus of the compact carbonate rock.

A method for experimentally determining the influence of acid liquor on the Young's modulus of compact carbonate rock, which sequentially comprises the following steps:

(1) selecting a standard core of a compact carbonate rock in a target work area for use, and carrying out a uniaxial compressive strength experiment to establish an empirical relationship between the uniaxial compressive strength and the Young's modulus of the compact carbonate rock;

(2) selecting a full-diameter core of the target work area, carrying out a rock scratching experiment by using a rock scoring instrument to test the compressive strength of the core, and acquiring the Young's modulus of the sample rock before acid treatment according to the empirical relationship between the compressive strength and the Young's modulus in step (1);

(3) sealing a portion of the full-diameter core, which never contacts the acid liquor, with potting glue, determining experimental conditions according to a reservoir temperature in the acid fracturing process, a fluid pressure in the crack, and an acid injection time, selecting an acid liquor system for acid fracturing in the field for use, and placing the acid liquor and the rock in a high temperature, and high pressure reactor for a soaking reaction; and (4) carrying out a scratching experiment again on the rock soaked with acid in the original scratching experiment position to test the compressive strength of the core, acquiring the young's module of the sample rock after acid treatment according to the empirical relationship between the compressive strength and the Young's modulus in the step (1), and comparing the Young's modulus of the sample core with the Young's modulus of the sample core before acid treatment to determine the influence of the acid liquor on the Young's modulus of the compact carbonate rock.

In the present invention, in the step (1), the step of selecting the standard core of the compact carbonate rock in the target work area for use, and carrying out the uniaxial compressive strength experiment to establish the empirical relationship between the uniaxial compressive strength and the Young's modulus of the compact carbonate rock comprises the following steps:

1) selecting the compact carbonate core in the target work area, and manufacturing the compact carbonate core into a standard cylindrical rock sample; placing the sample in an incubator for drying, and then carrying out a uniaxial experiment using a triaxial rock mechanics testing system to acquire the compressive strength and the Young's modulus of the core; and 2) testing the compressive strength and the Young's modulus of at least 10 core samples according to the method in 1), and establishing the following two empirical correlations between the compressive strength and the Young's modulus:

$$E = C_1 \sigma_c^{C_2} \quad (1)$$

$$E = C_1 \sigma_c + C_2 \quad (2)$$

determining $C_1$ and $C_2$ in the correlations and a correlation coefficient squared value $R^2$ according to the compressive strength and Young's modulus of the obtained samples and the empirical correlations between the compressive strength and the Young's modulus according to formula (1) or (2) by using a regression statistics method; comparing the $R^2$ values in the two regression formulas, selecting the empirical correlation corresponding to $R^2$ having the larger value as the empirical correlation between the compressive strength and Young's modulus of the research area, and requiring $R^2$ in the selected empirical correlation to be greater than 0.3; and in the case of the corresponding $R^2 \leq 0.3$ in the formula (1) and the formula (2), increasing the number of test samples until the requirement is satisfied.

In the present invention, in the step (2), the step of selecting the full-diameter core of the target work area, carrying out the rock scratching experiment by using the rock scoring instrument to test the compressive strength of the core, and acquiring the Young's modulus of the sample rock before acid treatment according to the empirical relationship between the compressive strength and the Young's modulus in step (1) comprises the following steps:

1) taking a diameter of the end surface of the full-diameter core as a reference line and forming two cutting lines perpendicular to the reference line, the two cutting lines being symmetric about the center of the circle; calibrating the diameter that passes through the center of the circle and is perpendicular to the reference line as a scratch line, carrying out a rock scratching experiment by using a rock scoring instrument to obtain the compressive strength distribution of the end surface of the core; and (2) acquiring the Young's modulus distribution of the tested core before acid treatment according to a compressive strength distribution profile, and the empirical relationship between the compressive strength and the Young's modulus determined in the step (1).

In the present invention, in the step (3), the step of sealing a portion of the full-diameter core, which never contacts the acid liquor, with potting glue, determining experimental conditions according to the reservoir temperature in the acid fracturing process, the fluid pressure in the crack, and the acid injection time, selecting the acid liquor system for acid fracturing in the field for use, and placing the acid liquor and the rock in the high temperature and high pressure reactor for a soaking reaction comprises the following steps:

1) preparation of the core before acid treatment: performing a glue sealing treatment on the core subjected to the scratch experiment, that is, encapsulating an unscratched end surface with potting glue, and exposing a scratched end surface;

2) setting of acid treatment experiment conditions: selecting an experimental acid liquor system as an acid liquor system used in the acid fracturing construction, wherein an experimental temperature is a crack temperature in the acid fracturing construction; an experimental time is an acid injection time; an experimental pressure is a difference between a fluid pressure and a formation pressure in the acid-fractured crack, wherein the determination method is as follows:

assuming that the acid-fractured crack extends according to a PKN model, the net pressure of the fluid in the acid-fractured crack is (edited by Eknomids, et al., translated by Zhang Baoping, et al, Reservoir Stimulation Measures (Third Edition) [M]. Petroleum Industry Press, 2002):

$$p - \sigma_{min} = \left[ \frac{16E^3 \mu QL}{\pi(1-\upsilon^2)^3 h^4} \right]^{1/4} \quad (3)$$

the fluid pressure in the acid-fractured crack is:

$$p = \left[ \frac{16E^3 \mu QL}{\pi(1-\upsilon^2)^3 h^4} \right]^{1/4} + \sigma_{min} \quad (4)$$

the difference between the fluid pressure and the formation pressure in the acid-fractured crack is:

$$\Delta p = \left[ \frac{16E^3 \mu QL}{\pi(1-\upsilon^2)^3 h^4} \right]^{1/4} + \sigma_{min} - p_e \quad (5)$$

the difference $\Delta p$ between the fluid pressure and the formation pressure in the acid-fractured crack in formula (5) is in a unit of the international SI unit system. After it is converted into the oilfield unit system, there is:

$$\Delta p = 1.502 \times 10^{-6} \left[ \frac{E^3 \mu QL}{(1-\upsilon^2)^3 h^4} \right]^{1/4} + \sigma_{min} - p_e \quad (6)$$

where, p is the fluid pressure in the acid-fractured crack, Pa; σmin is a minimum horizontal principal stress of the formation, MPa; E is the Young's modulus of the rock before contacting with acid liquor, Pa; μ is the viscosity of the acid liquor, Pa·s; Q is an acid injection displacement, m³/s; L is a crack length, m; υ is a Poisson's ratio of the rock, no dimension; h is a crack height, m; Δp is the difference between the fluid pressure and the formation pressure in the acid-fractured crack, MPa; $P_e$ is the formation pressure, Mpa; and 3) placing the acid liquor and the core in a high temperature and high pressure reactor to carry out high temperature and high pressure soaking experiments.

In the present invention, in the step (4), the step of carrying out a scratching experiment again on the rock soaked with acid in the original scratching experiment position to test the compressive strength of the core, acquiring the young's module of the sample rock after acid treatment according to the empirical relationship between the compressive strength and the Young's modulus in the step (1), and comparing the Young's modulus of the sample core with the Young's modulus of the sample core before acid treatment to determine the influence of the acid liquor on the Young's modulus of the compact carbonate rock comprises the following steps:

1) cleaning the core soaked with the acid liquor, and carrying out a scratching experiment again on the original end surface by using a rock scoring instrument, and recording compressive strength distribution data of the core;

2) acquiring the Young's modulus of the sample core after acid treatment according to the compressive strength distribution data and the empirical relationship between the compressive strength and the Young's modulus determined in the step (1); and 3) comparing the changes in the Young's modulus of the core before and after acid treatment to determine the influence of the acid liquor on the Young's modulus of the compact carbonate rock core.

Compared with the prior art, the present invention provides a method for experimentally determining the influence of the acid liquor on the Young's modulus of the compact carbonate rock. According to the method provided by the present invention, the changes in the Young's modulus of the same rock sample of the compact carbonate rock before and after acid treatment are accurately evaluated by way of combining a rock scoring instrument and a high temperature and high pressure reactor to provide reliable parameters for the design of the conductivity of acid-fractured cracks. This method overcomes the limitation that the existing methods cannot accurately evaluate the change in the Young's modulus of the compact carbonate rock during acid fracturing.

DETAILED DESCRIPTION

The present invention is further described in conjunction with the accompanying drawings and the application examples, and intended to exemplarily describe and explain the present invention, rather than limiting the scope of the present invention. Details are as follows:

(1) selecting a standard core of a compact carbonate rock in a target work area for use, and carrying out a uniaxial compressive strength experiment to establish an empirical relationship between the uniaxial compressive strength and the Young's modulus of the compact carbonate rock.

Figure 2:
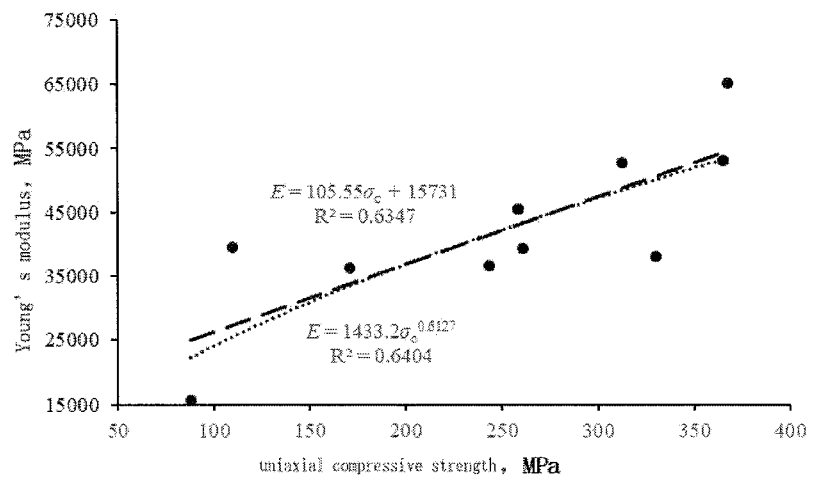
FIG. 2 is a graph showing the relationship between the Young's modulus and the uniaxial compressive strength of the rock in the present invention.

1) the compact carbonate rock core is selected from the target work area selected and manufactured into a standard cylindrical rock sample with a diameter of 25.4 mm and a length of about 50 mm; the standard cylindrical rock sample is placed in an incubator for drying, and then a uniaxial experiment is carried out using a triaxial rock mechanics testing system to obtain the compressive strength and the Young's modulus of the core; 2) the compressive strength and Young's modulus of at least 10 rock samples are tested according to the method in 1) to establish an empirical relationship between the compressive strength and the Young's modulus. Taking a compact carbonate reservoir in the Tarim Basin as an example, a uniaxial compression experiment of 10 cores is carried out using a triaxial rock mechanics testing system to acquire the compressive strength and the Young's modulus of the core. Fitting regression is performed according to Formula (1) and Formula (2). It is found that the squared value $R^2$ of the correlation coefficient is greater than 0.3, and the $R^2$ regressed according to Formula (1) is larger. Therefore, $E=1433.2\sigma_c^{0.6127}$ is selected as an empirical relation of Young's modulus calculation (see FIG. 2).

Figure 1:
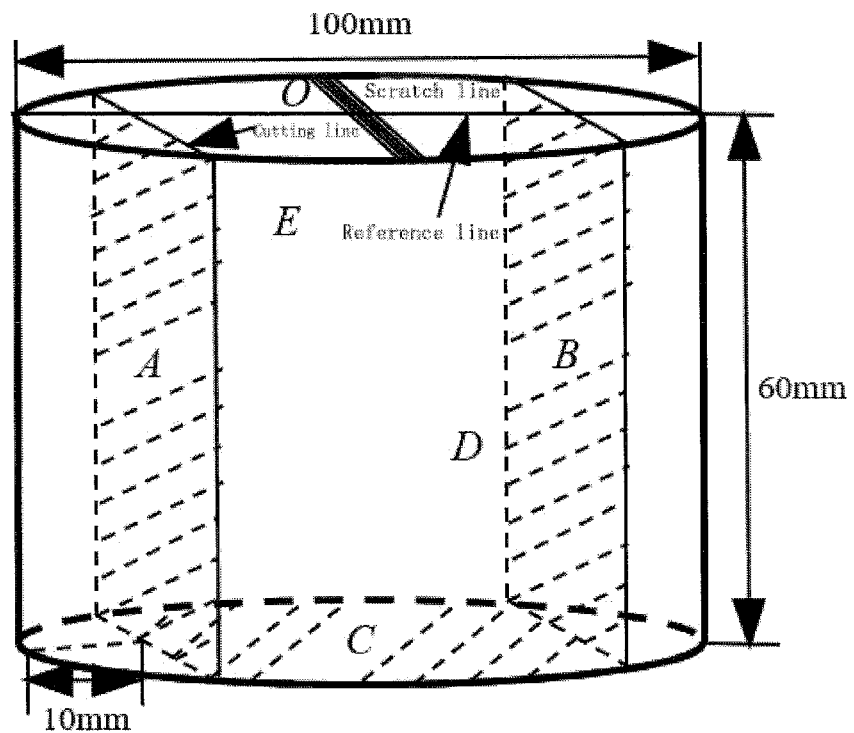
FIG. 1 is a schematic diagram showing the sample preparation of a full-diameter core in the present invention.

(2) Selecting a full-diameter core from the target work area, carrying out a rock scratching experiment by using a rock scoring instrument to test the compressive strength of the core, and acquiring the Young's modulus of the sample rock before acid treatment according to the empirical relationship between the compressive strength and the Young's modulus in step (1). The full-diameter core is selected from the research area to perform sample preparation according to the method in FIG. 1, the uniaxial compressive strength is tested with a rock scoring instrument (see FIG. 3), and the Young's modulus of the core before acid treatment is determined according to the established empirical correlation (see FIG. 4).

(3) Sealing a portion of the full-diameter core, which never contacts the acid liquor, with potting glue, determining experimental conditions according to a reservoir temperature in the acid fracturing process, a fluid pressure in the crack, and an acid injection time, selecting an acid liquor system for acid fracturing in the field for use, and placing the acid liquor and the rock in a high temperature and high pressure reactor for a soaking reaction.

The core subjected to the scratching experiment is encapsulated with potting glue, that is, the potting glue is applied on unscratched end surfaces (A, B, C, D, and E surfaces in FIG. 1), while a scratched end surface is exposed (O surface in FIG. 1), which is convenient for contact with acid liquor during experiments. A gelled acid system used in the construction of the work area is adopted as an experimental acid liquor system. The experimental temperature is 120° C. at which the acid liquor contacts the rock on the crack wall, and the soaking time in the acid liquor is an on-site acid injection time of 30 min Table 1 shows main parameters of the acid fracturing design. The difference between the fluid pressure and the formation pressure in the acid-fractured crack determined by data in Table 1 and Formula (6) is 21.7 MPa.

TABLE 1

| Part of basic parameters of acid fracturing design of a well | |
|---|---|
| Young's modulus of rock before contacting with acid liquor, E, Pa | $4.18835 \times 10^{10}$ |
| Poisson's ratio v of rock before contacting with acid liquor, no dimension | 0.26 |
| Minimum horizontal principal stress $\sigma_{min}$ of formation, MPa | 96.3 |
| Formation pressure $P_e$, MPa | 76.7 |
| Acid liquor viscosity μ, Pa · s | $3.0 \times 10^{-2}$ |
| Acid liquor injection displacement Q, m³/s | 0.1 |
| Acid-fractured crack length L, m | 100 |
| Acid-fractured crack height h, m | 50 |

According to the determined experimental parameters, the acid liquor soaking experiment is carried out using a high temperature and high pressure reactor.

(4) Carrying out a scratching experiment again on the rock soaked with acid in the original scratching experiment position to test the compressive strength of the core, acquiring the young's module of the sample rock after acid treatment according to the empirical relationship between the compressive strength and the Young's modulus in the step (1), and comparing the Young's modulus of the sample core with the Young's modulus of the sample core before acid treatment to determine the influence of the acid liquor on the Young's modulus of the compact carbonate rock.

Figure 3:
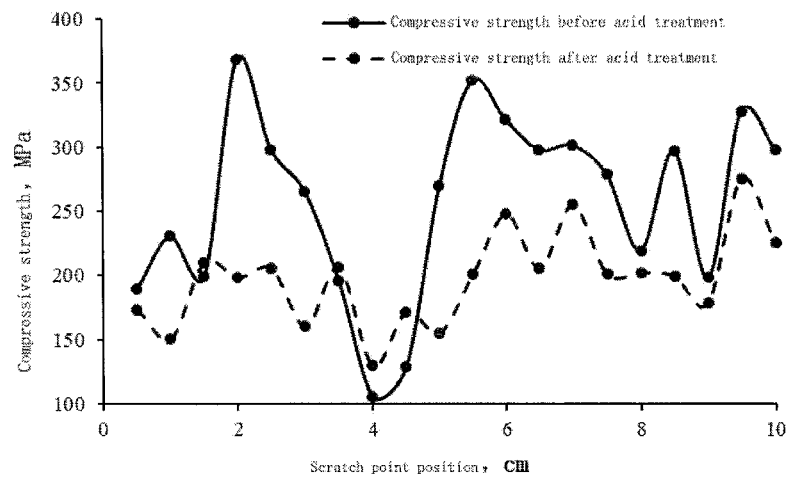
FIG. 3 is a graph showing the changes in compressive strength of the rock before and after acid treatment in the present invention.
Figure 4:
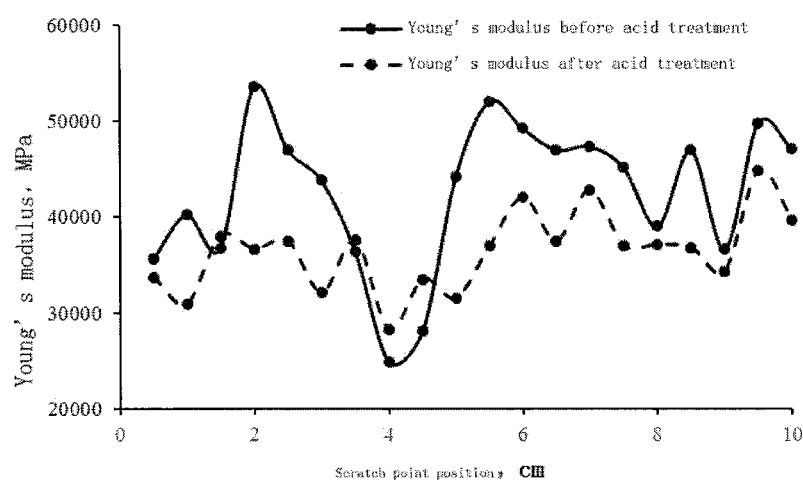
FIG. 4 is a graph showing the changes in Young's modulus of the rock before and after acid treatment in the present invention.

After the core soaked with acid is washed with water, the scratching experiment is continued at the original scratch to test the compressive strength of the core after acid treatment (see FIG. 3). The Young's module after acid treatment is determined according to the empirical relationship $E=1433.2\sigma_c^{0.6127}$ (FIG. 4). By comparison, it is found that the Young's modulus of the core has decreased to different extents at different locations, and the Young's modulus of the rock after acid treatment is used for the calculation of the conductivity in the acid fracturing design.

The invention claimed is:

1. A method for experimentally determining the influence of acid liquor on the Young's modulus of compact carbonate rock, which comprises the following steps:
   (1) selecting a standard core of a compact carbonate rock in a target work area for use, and carrying out a uniaxial compressive strength experiment to establish an empirical relationship between the uniaxial compressive strength and the Young's modulus of the compact carbonate rock;
   (2) selecting a full-diameter core of the target work area, carrying out a rock scratching experiment by using a rock scoring instrument to test the compressive strength of the core, and obtaining the Young's modulus of the sample rock before acid treatment according to the empirical relationship between the compressive strength and the Young's modulus in step (1);
   (3) sealing a portion of the full-diameter core, which never contacts the acid liquor, with potting glue, determining experimental conditions according to a reservoir temperature in the acid fracturing process, a fluid pressure in a crack, and the acid injection time, selecting an acid liquor system for acid fracturing in the field for use, and placing the acid liquor and the core in a high temperature and high pressure reactor for a soaking reaction; and
   (4) carrying out a scratching experiment again on the rock soaked with acid in the original scratching experiment position to test the compressive strength of the core, acquiring the young's module of the sample rock after acid treatment according to the empirical relationship between the compressive strength and the Young's modulus in the step (1), and comparing the Young's modulus of the sample core with the Young's modulus of the sample core before acid treatment to determine the influence of the acid liquor on the Young's modulus of the compact carbonate rock.

2. A method for experimentally determining the influence of the acid liquor on the Young's modulus of the compact carbonate rock according to claim 1, wherein the step (1) comprises the following steps:
1) selecting the compact carbonate core in the target work area, and manufacturing the compact carbonate core into a standard cylindrical rock sample; placing the sample in an incubator for drying, and then carrying out a uniaxial experiment using a triaxial rock mechanics testing system to obtain the compressive strength and the Young's modulus of the core; and
2) testing the compressive strength and the Young's modulus of at least 10 core samples according to the method in 1), and establishing the following two empirical correlations between the compressive strength and the Young's modulus:

$$E = C_1 \sigma_c^{C_2} \quad (1)$$

$$E = C_1 \sigma_c + C_2 \quad (2)$$

determining $C_1$ and $C_2$ in the correlations and a correlation coefficient squared value $R^2$ according to the acquired compressive strength and Young's modulus of the samples and the empirical correlations between the compressive strength and the Young's modulus according to formula (1) or (2) by using a regression statistics method; comparing the $R^2$ values in the two regression formulas, selecting the empirical correlation corresponding to $R^2$ having the larger value as the empirical correlation between the compressive strength and Young's modulus of a research area, and requiring $R^2$ in the selected empirical correlation to be greater than 0.3; and in case of the corresponding $R^2 \leq 0.3$ in the formula (1) and the formula (2), increasing the number of test samples until the requirement is satisfied.

3. A method for experimentally determining the influence of the acid liquor on the Young's modulus of the compact carbonate rock according to claim 1, wherein the step (2) comprises the following steps:
1) taking a diameter of the end surface of the full-diameter core as a reference line and forming two cutting lines perpendicular to the reference line, the two cutting lines being symmetric about the center of the circle; calibrating the diameter that passes through the center of the circle and is perpendicular to the reference line as a scratch line, carrying out a rock scratching experiment by using a rock scoring instrument to obtain the compressive strength distribution of the end surface of the core; and
(2) acquiring the Young's modulus distribution of the tested core before acid treatment according to a compressive strength distribution profile, and the empirical relationship between the compressive strength and the Young's modulus determined in the step (1).

4. A method for experimentally determining the influence of the acid liquor on the Young's modulus of the compact carbonate rock according to claim 1, wherein the step (3) comprises the following steps:
1) preparation of the core before acid treatment: performing a glue sealing treatment on the core subjected to the scratching experiment, that is, encapsulating an unscratched end surface with potting glue, and exposing a scratched end surface;
2) setting of acid treatment experiment conditions: selecting an experimental acid liquor system as an acid liquor system used in the acid fracturing construction, wherein an experimental temperature is a crack temperature in the acid fracturing construction; an experimental time is an acid injection time; an experimental pressure is a difference between a fluid pressure and a formation pressure in an acid-fractured crack:

$$\Delta p = 1.502 \times 10^{-6} \left[ \frac{E^3 \mu Q L}{(1-\upsilon^2)^3 h^4} \right]^{1/4} + \sigma_{min} - p_e$$

where, p is the fluid pressure in the acid-fractured crack, Pa; σmin is a minimum horizontal principal stress of the formation, MPa; E is the Young's modulus of the rock before contacting with acid liquor, Pa; μ is the viscosity of the acid liquor, Pa·s; Q is an acid injection displacement, m³/s; L is a crack length, m; υ is a Poisson's ratio of the rock, no dimension; h is a crack height, m; Δp is the difference between the fluid pressure and the formation pressure in the acid-fractured crack, MPa; $P_e$ is a formation pressure, Mpa; and
3) placing the acid liquor and the core in a high temperature and high pressure reactor to carry out a high temperature and high pressure soaking experiment.

5. A method for experimentally determining the influence of the acid liquor on the Young's modulus of the compact carbonate rock according to claim 1, wherein the step (4) comprises the following steps:
1) cleaning the core soaked with the acid liquor, and carrying out a scratching experiment again on the original end surface by using a rock scoring instrument, and recording compressive strength distribution data of the core;
2) acquiring the Young's modulus of the core after acid treatment according to the compressive strength distribution data and the empirical relationship between the compressive strength and the Young's modulus determined in the step (1); and
3) comparing the changes in the Young's modulus of the core before and after acid treatment to determine the influence of the acid liquor on the Young's modulus of the compact carbonate rock core.

* * * * *